United States Patent [19]

Chaglassian

[11] Patent Number: 4,773,909
[45] Date of Patent: * Sep. 27, 1988

[54] MULTI-LUMEN HIGH PROFILE MAMMARY IMPLANT

[75] Inventor: Toros A. Chaglassian, Forest Hills Garden, N.Y.

[73] Assignee: Memorial Hospital for Cancer and Allied Diseases, New York, N.Y.

[*] Notice: The portion of the term of this patent subsequent to Mar. 17, 2004 has been disclaimed.

[21] Appl. No.: 939,567

[22] Filed: Dec. 9, 1986

Related U.S. Application Data

[63] Continuation of Ser. No. 309,142, Oct. 6, 1981, Pat. No. 4,650,487, which is a continuation-in-part of Ser. No. 200,837, Oct. 27, 1980, abandoned.

[51] Int. Cl.$^4$ ............................................. A61F 2/12
[52] U.S. Cl. .......................................... 623/8; 623/7; 623/11
[58] Field of Search ................. 623/7, 8, 11; 128/1 R

[56] References Cited

U.S. PATENT DOCUMENTS

| | | | |
|---|---|---|---|
| 2,431,878 | 12/1947 | McGregor | 260/46.5 |
| 2,541,851 | 2/1951 | Wright | 260/37 |
| 2,636,182 | 4/1953 | Freedman | 3/36 |
| 2,842,775 | 7/1958 | Pangman | 3/36 |
| 3,020,260 | 2/1962 | Nelson | 260/46.5 |
| 3,067,431 | 12/1962 | Kausch | 3/36 |
| 3,189,921 | 6/1965 | Pangman | 3/36 |
| 3,293,663 | 12/1966 | Cronin | 3/36 |
| 3,366,975 | 2/1968 | Pangman | 3/36 |
| 3,445,420 | 5/1969 | Kookootsedes | 260/37 |
| 3,559,214 | 2/1971 | Pangman | 3/36 |
| 3,600,718 | 8/1971 | Boone | 3/36 |
| 3,665,520 | 5/1972 | Perras | 3/36 |
| 3,681,787 | 8/1972 | Perras | 623/8 |
| 3,683,424 | 8/1972 | Pangman | 3/36 |
| 3,852,832 | 12/1974 | McGhan | 3/36 |
| 3,852,833 | 12/1974 | Koeneke et al. | 3/36 |
| 3,860,969 | 1/1975 | Arion | 3/36 |
| 3,883,902 | 5/1975 | Lynch | 3/36 |
| 3,902,198 | 9/1975 | Rathjen | 3/36 |
| 3,919,724 | 11/1975 | Saunders | 3/36 |
| 3,934,274 | 1/1976 | Hartley | 623/8 |
| 3,986,213 | 10/1976 | Lynch | 3/36 |
| 4,125,117 | 11/1978 | Lee | 3/36 |
| 4,178,643 | 12/1979 | Cox, Jr. | 3/36 |
| 4,205,401 | 6/1980 | Frisch | 623/8 |
| 4,264,990 | 5/1981 | Hamas | 3/36 |
| 4,298,998 | 11/1981 | Naficy | 623/8 |
| 4,605,412 | 8/1986 | LaForest et al. | 623/8 |

FOREIGN PATENT DOCUMENTS

| | | | |
|---|---|---|---|
| 5275 | 11/1979 | European Pat. Off. | 3/36 |
| 2199266 | 4/1974 | France | 623/8 |
| 933052 | 7/1963 | United Kingdom | 3/36 |

OTHER PUBLICATIONS

Courtiss, E. H., M.D. et al., "Selection of Alternatives in Augmentation and Mammaplasty", *Plastic and Reconstructive Surgery*, Nov. 1974.

(List continued on next page.)

Primary Examiner—Richard J. Apley
Assistant Examiner—David Isabella
Attorney, Agent, or Firm—John P. White

[57] ABSTRACT

A surgically implantable, multi-lumen, high profile mammary implant includes a first, flexible, lumen at least partly and filled with a soft gel material and having a front wall approximating the shape of a human breast and a second, firmer flexible lumen elastic within the first lumen and connected thereto solely at the rear wall of the first lumen. The second lumen has a volume which is less than the volume of the first lumen and at least partly filled with a second soft gel material. A third lumen preferably inflatably surrounds the first lumen and is inflated with saline solution. The second lumen is made firmer than any other lumen of the implant by providing it with a greater percent fill than any other lumen of the multi-lumen implant, filling it with a material which has a greater density than any materials filling any other lumen of the implant, providing it with thicker walls than any other lumen, or by filling it with material which has a greater crosslink density than the materials filling any of the other lumens. The multi-lumen, structure has a high profile implant which is most suitable for breast reconstruction.

5 Claims, 1 Drawing Sheet

OTHER PUBLICATIONS de Cholonoky, T., M.D., "Augmentation Mammaplasty," *Plastic and Reconstructive Surgery,* Jun., 1970.

Rees, T. D., M.D., et al., "The Use of Inflatable Breast Implants", *Plastic and Reconstructive Surgery,* 1973.

Regnault, P. C., M.D., "The Hypoplastic and Ptotic Breast: A Combined Operation with Prosthetic Augmentation", *Plastic and Reconstructive Surgery,* Jan., 1966.

Regnault, P. C., M.D., "Indications for Breast Augmentation", *Plastic and Reconstructive Surgery,* Dec., 1967.

Snyderman, R. K., M.D., et al., "Reconstruction of the Female Breast Following Radical Mastectomy", *Plastic and Reconstructive Surgery,* Jun., 1971.

"Two-Lumen Mammary Implants", McGhan Medical Corporation, 1977.

Williams, J. E., M.D. "Experiences with a Large Series of Silastic Breast Implants", *Plastic and Reconstructive Surgery,* Mar., 1972.

Dow Corning, (Oct. 1977) Bulletin 51.226 Silastic Mammary Prosthesis (Round Design).

MULTI-LUMEN HIGH PROFILE MAMMARY IMPLANT

This application is a continuation application of application Ser. No. 309,142, filed Oct. 6, 1981, now U.S. Pat. No. 4,650,487, which in turn was a continuation-in-part of copending application Ser. No. 200,837, filed Oct. 27, 1980 now abandoned.

BACKGROUND OF THE INVENTION

The present invention relates to a surgically implantable prosthesis and more specifically to a multi-lumen high profile mammary implant.

Mammary implants are known in the prior art as evidenced by U.S. Pat. Nos. 2,842,775; 3,189,921; 3,293,663; 3,366,975; 3,559,214; 3,665,520; 3,683,424; 3,852,832; 3,860,969; 3,883,902; 3,902,198; 3,919,724; and 3,986,213.

These aforementioned prior art patents show the advances made, especially in the materials constituting the implant including the silicone envelope for the implant and the silicone gel filler as disclosed for example in U.S. Pat. Nos. 2,431,878; 2,541,851; 3,020,260; and 3,445,420.

Major problems with the mammary implants made in accordance with the prior art disclosures are the lack of projection and the eventual distortion of the implant, both of which provide a cosmetically unattractive result. Several advances have been made to overcome these problems as set forth in U.S. Pat. No. 3,681,787, which utilizes a single container filled with gels of different densities and U.S. Pat. No. 3,934,274, which utilizes an inner and outer container or lumen constituting the implant device.

A two-lumen mammary implant is currently marketed by McGhan Medical Corporation which includes an inner silicone envelope which is filled with silicone gel and an outer silicone elastomer inflatable shell which is initially unfilled and is filled upon use with a normal saline to adjust the total volume of the implant. The implant includes a posterior leaf valve for filling the outer shell.

Despite the advances made as indicated by the prior art patents, the implants still have the disadvantage of not providing high projection and in certain cases not maintaining their desired shape after implantation.

SUMMARY OF THE INVENTION

The main object of the present invention is to overcome the disadvantages of the prior art implants and provide an implant which is soft, has high projection, and maintains its shape during use. By "high projection" it is meant that the implant of the present invention when placed on a horizontal surface has a projection to weight ratio when projection is measured vertically from the center of the implant of at least about 0.1 mm/gm based on the entire weight of the implant.

These and other objects are achieved in accordance with the present invention by providing a surgically implantable multi-lumen, high profile mammary implant comprising:

a first flexible lumen having a front wall with an outer shape capable of approximating the shape of the human breast, and a rear wall with an outer shape capable of approximating the shape of the human chest wall, and filled with a soft gel material; and a second flexible lumen within the first lumen wherein the second lumen occupies less than the entire volume of the first lumen, is filled with a soft gel material, and is firmer than the first lumen so as to provide the implant with a projection to weight ratio of at least about 0.1 mm/gm, and preferably from about 0.15 to 0.3 mm/gm.

An implant having this projection has a height to base diameter ratio, when height is measured from the center of the implant, of at least about 0.5/1. The second or innermost lumen is made firmer than any other lumen by means which include providing the innermost lumen with a greater percent fill than any of the outer lumens, providing the soft material filling the innermost lumen with higher density than the materials filling any of the other lumens, and/or providing the material filling the innermost lumen with a greater crosslink density than the materials filling any of the other lumens. Additional means of ensuring that the innermost lumen be firmer than any of the other lumens are also contemplated and fall within the scope of the instant invention.

The multi-lumen implant of the present invention may be used for breast augmentation or reconstruction, but due to its high projection and improved dimensional stability, finds particular use in breast reconstruction.

These and other features and advantages of the present invention will become apparent from consideration of the following specification when taken in conjunction with the accompanying drawings wherein:

DETAILED DESCRIPTION OF THE PREFERRED EMBODIMENTS

Figure 1:
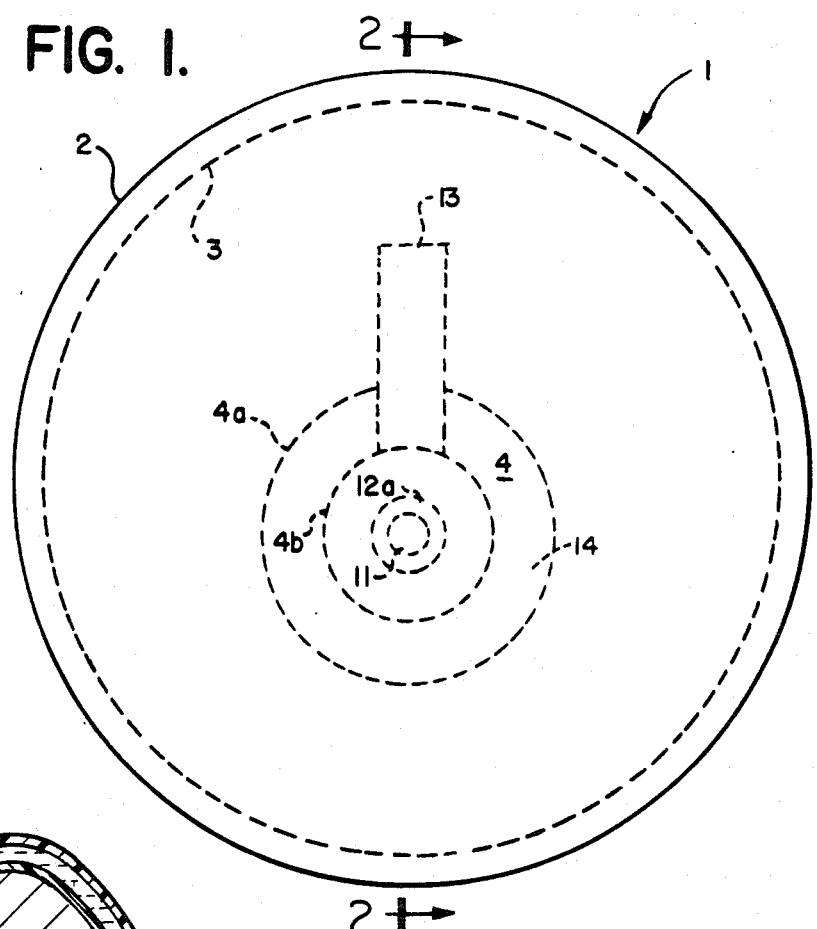
FIG. 1 is a front view of the implant made in accordance with the present invention.
Figure 2:
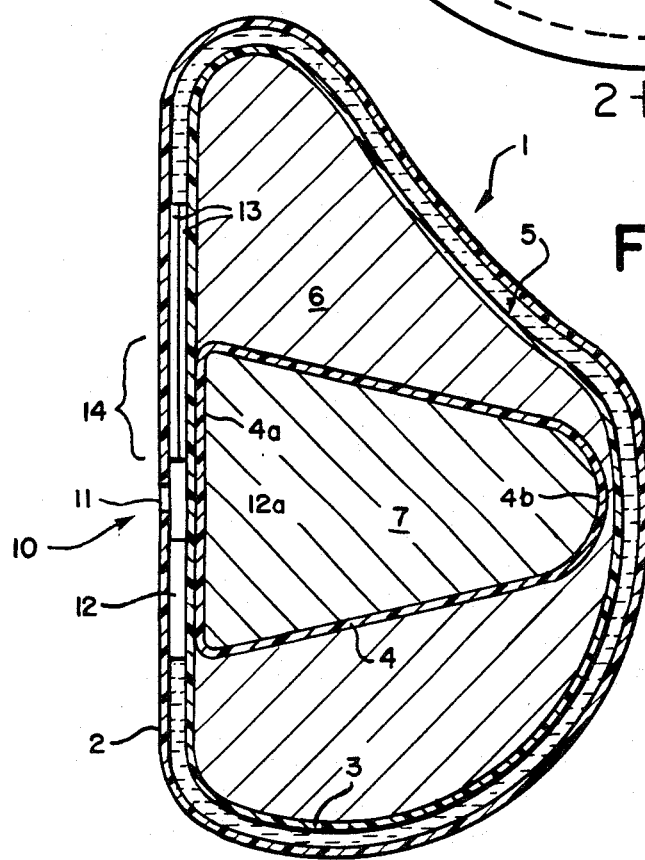
FIG. 2 is a cross-sectional view of the implant of FIG. 1 along line 2—2.

Referring to FIGS. 1 and 2, a tri-lumen mammary implant 1 according to the present invention is portrayed. It is understood that while a tri-lumen implant is illustrated, a bi-lumen implant or an implant having more than three lumens is also contemplated, provided that at least two of the lumens have the relative configurations and firmness to be capable of providing the implant with a projection to weight ratio of at least about 0.1 mm/gm.

The implant 1 includes a silicone envelope or lumen 3 which is filled with silicone gel of the type disclosed in U.S. Pat. No. 3,020,260. While the envelope 3 is flexible and the gel 6 is soft, the envelope 3 has a "fixed" volume (one of which is not changed in use) so that it may assume a shape as shown in FIG. 2 having a substantially planar rear wall to conform to the shape of the human chest wall and has a remaining contour thereof approximating the shape of the human breast. While the shape of envelope 3 is of a so-called "round" configuration, it is well understood by those skilled in the art that the filled envelope 3 can be configured in various other desired shapes such as a "tear drop" or oval low profile.

Disposed around the envelope 3 is an outermost silicone elastomer inflatable envelope or lumen 2. Envelope 2 is preferably also round and fillable with physiologic fluid such as normal saline to adjust the total volume of the implant. Alternatively envelope 2 may be filled with other typical liquids which are compatible with the human body. The configuration of the envelope 2 after filling is shown in FIG. 2 wherein the rear wall thereof approximates the shape of the human chest wall, while the frontal portion approximates the shape of the human breast in conformity with the shape of envelope 3.

Outermost envelope 2 may be inflated with liquid after implantation and subsequently deflated by removal of liquid to relieve the effects of spherical contraction of surrounding tissue on the implant.

The envelopes 2 and 3 are interconnected at the rear wall thereof with valve means 10 disposed therebetween to enable the fluid to be inserted to fill the volume 5 between envelopes 2 and 3. The two envelopes 2 and 3 are connected in an annular region 14 by heat sealing techniques or the like.

Disposed within envelope 3 and connected thereto solely at the rear walls thereof is innermost envelope or lumen 4 which occupies less than the entire volume of envelope 3. Envelope 4 comprises substantially the same material as flexible envelope 3 and is preferably a silicone envelope having a "fixed" volume (one which is not changed in use) and filled with a soft gel material 7, such as the aforementioned silicone gel. In accordance with the invention, an envelope 4 is firmer than intermediate envelope 3, to provide implant 1 with high projection and orientational stability. Innermost envelope 4 is made firmer than intermediate envelope 3 preferably by providing envelope 4 with a higher percent fill than envelope 3. Optionally, but preferably, envelope 4 has walls which are thicker than the walls of any of the other lumens. In particular the percent fill of envelope 4 is preferably at least about 1.1 times the percent fill of intermediate envelope 3, and most preferably between about 1.1 and 4.0 times the percent fill of envelope 3. Preferably the percent fill of envelope 4 is about 80 to 150 percent, based on the initial, unfilled of envelope 4, and most preferably the percent fill of envelope 4 is between about 90 to 120 percent. Alternatively, envelope 4 is made firmer than envelope 3 by providing that material 7 within the innermost envelope 4 has a higher density than that of the material 6 in envelope 3. In particular, the density of the material 7 should be from about 1.01 to 1.4 times the density of the material 6 and preferably about 1.1 times the density. Yet another alternative is to make envelope 4 firmer by providing that material 7 within envelope 4 has a greater crosslink density than that of material 6 in envelope 3. Preferably the crosslink density of material 7 is at least about 1.02 times the crosslink density of material 6, and most preferably it is about 1.1 times the crosslink density of material 6. It is understood that various combinations of the above technologies can be used to achieve the desired firmness.

The innermost lumen 4 has a frusto-conical configuration having a rounded tip 4b and a flat base 4a connected to the rear wall of lumen 3.

The gel material 6 and 7 is normally crosslinked dimethylpolysiloxane as disclosed in U.S. Pat. No. 3,020,260, however, it is recognized that other materials may be equally suitable so long as the consistency and viscosity of the implant material closely simulates the contours and characteristics of the human breast. The preferred gel is comprised of about 5-20 parts by weight, with 8 parts by weight being particularly preferred of

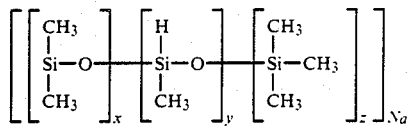

and from 80 to about 95 parts by weight, with 92 parts by weight being particularly preferred of

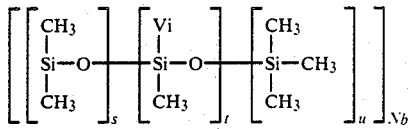

wherein s is about 162, t is about 1, u is about 2, x is about 172, y is about 6, z is about 2, $N_a$ is about 180 and $N_b$ is about 165. The preferred crosslinker is polymethyl 'H'-siloxane in a concentration of about 8 to 17 parts per hundred. While the preferred concentration of the crosslinker is about 8.2 where the innermost lumen is made firmer by filling it to a greater degree than any of the other lumens, when it is desired to make the innermost lumen firmer by providing that the material in the innermost lumen have a greater crosslink density, the concentration of the crosslinker may be increased up to about 17 parts per 100.

The walls of envelopes 2, 3 and 4 are generally between about 0.05 mm and 0.2 mm in thickness. Although, according to a particularly preferred embodiment the walls of envelope 4 are thicker than the walls of envelopes 2 and 3, preferably between about 0.3 mm and 0.4 mm in thickness.

The walls of envelopes 2, 3 and 4 may be constructed of any soft, flexible materials known in the art such as silicone rubber. The primary criterion for the walls are that they are capable of containing the material therein and that the complete implant is soft, pliable and comfortable and be capable of assuming natural body contours. Preferred materials for construction of the walls of envelopes 2 and 3 are silicone elastomers including homopolymers such as polydimethylsiloxane or polymethylvinylsiloxane, or copolymers such as copolymers of methylvinylsiloxane and dimethylsiloxane. A particularly preferred material for construction of the walls of envelopes 2 and 3 is a heteropolymer of diphenylsiloxane and dimethylpolysiloxane having 3-7 mole percent diphenylpolysiloxane substituents.

The silicone elastomers may also contain fillers, such as reinforcing silica filler, processing aids, additives, pigments. The fillers may be present in amounts of up to 70 parts per hundred by weight. The silicone elastomers are endblocked with conventional endblocking units present at levels of less than 4 mole percent. Examples of such endblocking units are dimethylvinylsiloxane units, trimethylsiloxy units, methylphenylvinylsiloxy units or hydroxyl units. In the present invention, 0.133 mole percent dimethylvinyl-siloxane units is preferred for this purpose.

The silicone elastomer can be vulcanized by conventional means, such as with organic peroxides, electromagnetic radiation, or by using a polysiloxane crosslinker containing silicone-bonded hydrogen atoms with a vinyl containing siloxane elastomer and a platinum catalyst. In the present invention it is preferred that a platinum catalyst formed by dissolving hexachloroplatinic acid with tetravinylcyclotetrasiloxane in isopropyl alcohol be used.

The walls of envelope 4 may be constructed from any material which is suitable for the construction of the walls of envelopes 2 and 3. Preferably, however, the walls of envelope 4 are comprised of a layer of silicone elastomer which substantially impedes the migration of the silicone gel from the sac. This layer is at least 0.025 mm in thickness and experiences a weight increase of less than 10% when tested in accordance with ASTM D471 utilizing a dimethylpolysiloxane test gel having a 300 centistoke viscosity.

Preferably the walls of envelope 4 are a composite structure of a plurality of silicone elastomers or mixtures of silicone elastomers which have a total thickness of between about 0.05 and about 0.4 mm, wherein at least one layer of the total composite wall is the migration impeding layer described hereinabove. Alternatively, the migration impeding layer may constitute the entire wall of envelope 4. Most preferably the composite wall of envelope 4 is comprised of three continuous layers. Although either of the three layers can be made to impede the migration of silicone gel through the envelope 4, it is preferred that the second or intermediate layer be constituted to do so by the means which are discussed below.

The silicone elastomers utilized for the first and third continuous layers may be any of the silicone elastomers which are suitable for the construction of the walls of envelopes 2 and 3 and is preferably a heteropolymer of diphenylpolysiloxane and dimethylpolysiloxane having 3-7 mole percent diphenyl polysiloxane substituents endblocked with 0.133 mole percent dimethylvinylsiloxane units.

The silicone elastomer of the second migration impeding layer is preferably composed of a reaction product of dimethylpolysiloxane and either 3,3,3-trifluoropropylpolysiloxane, diphenylpolysiloxane or methylphenylpolysiloxane. The final reaction product preferably contains about 8 to about 50 mole percent diphenylpolysiloxane substituents, with about 15 to about 30 being preferred, at least 90 mole percent methyl 3,3,3-trifluoropropylpolysiloxane substituents or at least 30 mole percent methylphenylplysiloxane substituents. It is contemplated that the silicone elastomer which acts as a barrier to migration may also be a reaction product of dimethylpolysiloxane and siloxane elastomer which has a combination of the aforementioned substituents, e.g., diphenylpolysiloxane and 3,3,3-trifluoropropylpolysiloxane. In a particularly preferred embodiment the migration impeding layer is composed of a reaction product of dimethylpolysiloxane and diphenylpolysiloxane, with about 15 mole percent diphenylpolysiloxane substituents.

The silicone elastomers of the migration impeding layer are endblocked with the conventional endblocking units used in the elastomers comprising the walls of envelopes 2 and 3 at levels of less than 4 mole percent. In the present invention, 0.133 mole percent dimethylvinylsiloxane units is preferred for this purpose.

The silicone elastomers comprising any of the layers of the preferred composite wall of envelope 4 can also contain fillers, such as reinforcing silica filler, processing aids, additives and pigments. The filler may be present in about 15 to about 70 parts per hundred by weight. The silicone elastomer can be vulcanized by conventional means, such as with organic peroxides, electromagnetic radiation, or by using a polysiloxane cross-linker containing silicone-bonded hydrogen atoms with a vinyl containing siloxane elastomers and a platinum catalyst. In the present invention it is preferred that the same platinum catalyst utilized for the walls of envelopes 2 and 3 be used.

The preferred shape of the inner envelope 4 is that of a cone section having the tip 4b rounded and projecting outwardly to the front of the implant, and the base 4a being the only portion of the envelope 4 connected to the envelope 3 and being fixed thereto in the aforementioned annular region 14. This assures that when the implant is fixed to the chest wall of the patient, the firmer, more fully filled portion defined by envelope 4 will project outwardly therefrom and will be less influenced by any deformations caused by the forces acting on the frontal portion of envelopes 2 and 3. In this way, the implant will have high projection and will retain its shape despite the distorting forces which traditionally render the implants aesthetically unattractive.

It is therefore clear that the tip portion 4b of the inner envelope 4 should be only slightly spaced from the front portion of envelope 3 but not connected thereto so as to provide for relative movement therebetween.

For a conventional size implant, the volume of material 6 is from about 100 to 600 cc while the volume of the inner envelope 4 is from about 20 to 300 cc, and is preferably about 30 to 100 cc. The volume 5 within the inflatable envelope 2 can be conventionally up to about 100 cc and is preferably filled with a normal saline.

The valve means 10 is formed by a valve member 12 which is disposed between the envelopes 2 and 3 and which has a protruding leaves 13 which extend beyond the sealed area 14 and into the volume 5 between envelopes 2 and 3. The leaf valve member 12 has a central opening 12a and the outer envelope 2 has a small opening 11 aligned with opening 12a which permits access to leaves 13.

In use, a fill tube is inserted by pointing the tube into the openings 11 and 12a allowing penetration through the leaves 13 of the valve so that it protrudes therefrom into the volume 5 between envelopes 2 and 3. The normal saline is filled to the desired volume and the fill tube is retracted from the valve which thereupon closes due to the forces on the leaves 13.

The tri-lumen implant of the present invention is preferably constructed according to the following procedure. Dispersions of the above stated unvulcanized elastomeric materials in solvents which can be totally evaporated from the final product at low temperatures e.g., 25° C. are made. When the silicone elastomer contains diphenylpolysiloxane substituents the solvents may be any aromatic or linear aliphatic of $C_6$ or greater. If the silicone elastomer contains trifluoropropylpolysiloxane substituents, the preferred solvents are ketones. Each envelope is prepared by dipping a mandrel which is shaped to the desired form into a dispersion of the desired unvulcanized silicone elastomer. The coated mandrel is removed and the solvent allowed to evaporate. The coated mandrel is then dipped into other dispersions of unvulcanized silicone elastomers until the desired composite structure is formed. The solvent is allowed to evaporate after each coating. All coats are preferably cured together after the coating has been built up to yield the desired post-cure thickness of between 0.05 mm and 0.2 mm. At this thickness the cured shell is soft, flexible and preferably elastic. Although the curing may occur at room temperture, it is preferably accelerated by the use of an air circulating oven.

After the silicone elastomer envelope has been cured, it is removed from the mandrel by stretching the hole at the mandrel attachment site. The envelopes are then placed one inside the other. The holes in each envelope are then sealed by cementing a patch of a laminate comprised of cured and uncured silicone elastomer of the same type as the envelope over and overlapping the periphery of the hole. Valve member 12 with protruding leaves 13 is then inserted between envelopes 2 and 3. The envelopes of the tri-lumen implant are then heat vulcanized together at the patch sites. Subsequently, an uncured and hence liquid silicone gel is injected, with the aid of a hypodermic needle through the patch site into innermost envelope 4. Liquid silicone gel is then injected in the same manner into envelope 3. The gels are then thermally cured. Prior to curing, the hypodermic entrance is sealed by applying a dimethylpolysiloxane having an alkoxy or oxime curing system, e.g. Dow Corning Medical Adhesive Silicone Type A, a room temperature vulcanizing adhesive.

It will be understood that the particular embodiments of the invention shown herein are by way of illustration only and are meant to be in no way restricted and that numerous changes and modifications can be made and the full use of equivalence resorted to without departing from the spirit and scope of the invention defined by the foregoing claims.

What is claimed is:

1. A multi-lumen mammary implant which is soft, will maintain its desired shape after implantation and has high projection, said implant comprising first and second lumens, said second lumen being contained within said first lumen, wherein the first lumen has a front wall with an outer shape for approximating the shape of the human breast and a rear wall with an outer shape for approximating the shape of the human chest wall, the second lumen has walls including a rear wall and is connected to the first lumen at the rear wall of each lumen, the first lumen contains the second lumen and, between the first and second lumens, a first soft gel, the second lumen contains a second soft gel, the second soft gel having a higher density than the first soft gel, thereby rendering the second gel-containing lumen as a whole more firm than the gel-containing first lumen.

2. A multi-lumen mammary implant which is soft, will maintain its desired shape after implantation and has high projection, said implant comprising first and second lumens, said second lumen being contained within said first lumen, wherein the first lumen has a front wall with an outer shape for approximating the shape of the human breast and a rear wall with an outer shape for approximating the shape of the human chest wall, the second lumen has walls including a rear wall and is connected to the first lumen at the rear wall of each lumen, the first lumen contains the second lumen and, between the first and second lumens, a first soft gel, the second lumen contains a second soft gel, the second soft gel having a greater crosslink density than the first soft gel, thereby rendering the second gel-containing lumen as a whole more firm than the gel-containing first lumen.

3. The implant of either of claims 1 or 2, wherein the implant includes a inflatable third lumen having a flexible front wall with an outer shape for approximating the shape of the human breast, a rear wall with an outer shape for approximating the shape of the human chest wall, and containing the first lumen, wherein the third lumen comprises valve means permitting inflation and deflation of space between the first and third lumens and, in the space between the first and third lumens, contains a liquid compatible with the human body.

4. The implant of either of claims 1 or 2, wherein the second lumen has a greater percent of fill or gel than the first lumen.

5. The implant of either of claims 1 or 2, wherein the second lumen has firmer walls than the first lumen.

* * * * *